US007238188B2

(12) United States Patent
Nesper et al.

(10) Patent No.: US 7,238,188 B2
(45) Date of Patent: Jul. 3, 2007

(54) IMPLANT FOR FIXING BONE PLATES

(75) Inventors: Markus Nesper, Tuttlingen (DE);
Klaus-Dieter Steinhilper, Tuttlingen (DE); Dieter Weisshaupt, Immendingen (DE)

(73) Assignee: Aesculap AG & Co. KG, Tuttlingen (DE)

( * ) Notice: Subject to any disclaimer, the term of this patent is extended or adjusted under 35 U.S.C. 154(b) by 596 days.

(21) Appl. No.: 10/718,851

(22) Filed: Nov. 20, 2003

(65) Prior Publication Data
US 2004/0102779 A1 May 27, 2004

Related U.S. Application Data

(63) Continuation of application No. PCT/EP02/05653, filed on May 23, 2002.

(30) Foreign Application Priority Data
Jun. 15, 2001 (DE) ................. 101 28 917

(51) Int. Cl.
*A61B 17/56* (2006.01)
*A61B 17/58* (2006.01)
(52) U.S. Cl. ........................ 606/72; 606/232
(58) Field of Classification Search .............. 606/72, 606/75, 232, 213, 70, 71, 69, 60, 215
See application file for complete search history.

(56) References Cited

U.S. PATENT DOCUMENTS

| 2,576,649 | A |   | 11/1951 | Slind |
| 4,802,477 | A |   | 2/1989  | Gabbay |
| 5,021,059 | A |   | 6/1991  | Kensey et al. |
| 5,423,858 | A |   | 6/1995  | Bolanos et al. |
| 5,464,427 | A | * | 11/1995 | Curtis et al. ............... 606/232 |
| 5,601,557 | A | * | 2/1997  | Hayhurst .................... 606/72 |
| 5,800,436 | A |   | 9/1998  | Lerch |
| 5,921,986 | A |   | 7/1999  | Bonutti |
| 6,022,351 | A |   | 2/2000  | Bremer et al. |
| 6,726,688 | B2 | * | 4/2004  | Lerch ......................... 606/72 |
| 6,921,401 | B2 | * | 7/2005  | Lerch et al. ................. 606/72 |
| 7,048,737 | B2 | * | 5/2006  | Wellisz et al. ............... 606/70 |
| 2002/0156475 | A1 |   | 10/2002 | Lerch et al. |

FOREIGN PATENT DOCUMENTS

| DE | 2 125 556  | 5/1971  |
| DE | 296 14 921 | 11/1996 |
| DE | 299 19 090 | 1/2000  |
| DE | 198 32 797 | 2/2000  |
| EP | 0 787 466  | 8/1997  |
| WO | 00/49949   | 8/2000  |

OTHER PUBLICATIONS

*Patent Abstracts of Japan*, Abstract of Japanese Patent "Cranio-Knochenschallapen Fixing Device", Publication No. 05220174, Aug. 31, 1993, Japanese Application No. 04056619, Filed Feb. 10, 1992.

* cited by examiner

*Primary Examiner*—Pedro Philogene
(74) *Attorney, Agent, or Firm*—Lipsitz & McAllister, LLC

(57) ABSTRACT

In an implant for fixing neighboring bone plates of the cranial bone comprising an inner bearing element which covers a spacing gap between the bone plates, an outer bearing element which covers the spacing gap and a connecting device which penetrates the spacing gap and which, when said bearing elements approach one another, connects the bearing elements together by means of a latching or a clamping connection in such a manner that they are no longer able to be moved apart, it is proposed that the two bearing elements be additionally connected by a thread-like tensioning element which is passed through the outer bearing element in displaceable manner and, when tensioned, moves the inner bearing element towards the outer bearing element in order to simplify the process of applying the implant and to ensure a secure connection of the bearing elements.

25 Claims, 2 Drawing Sheets

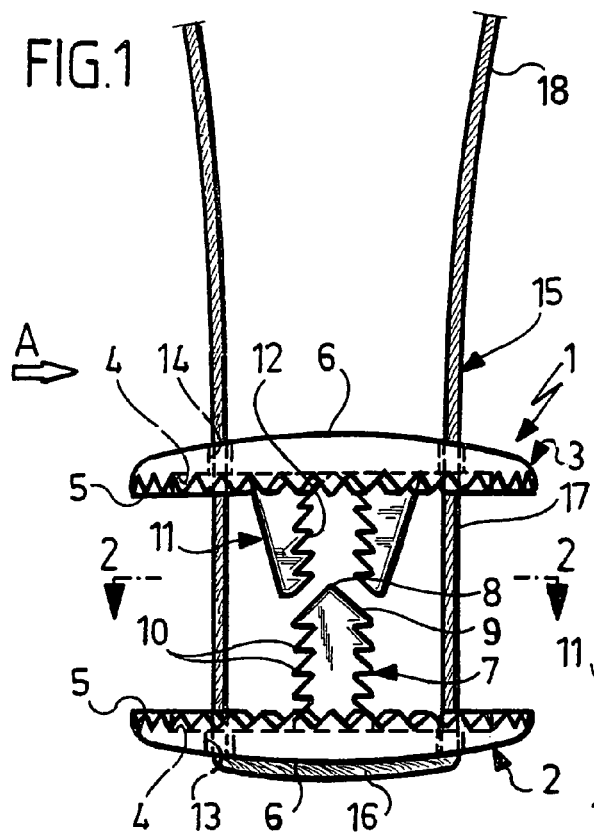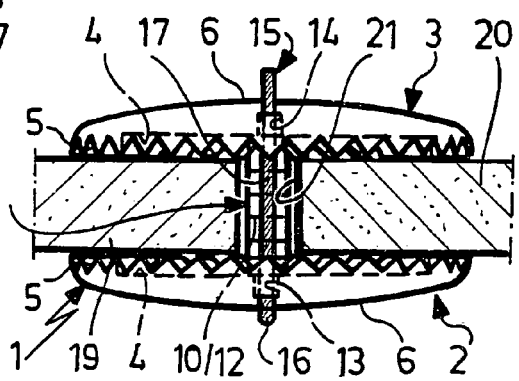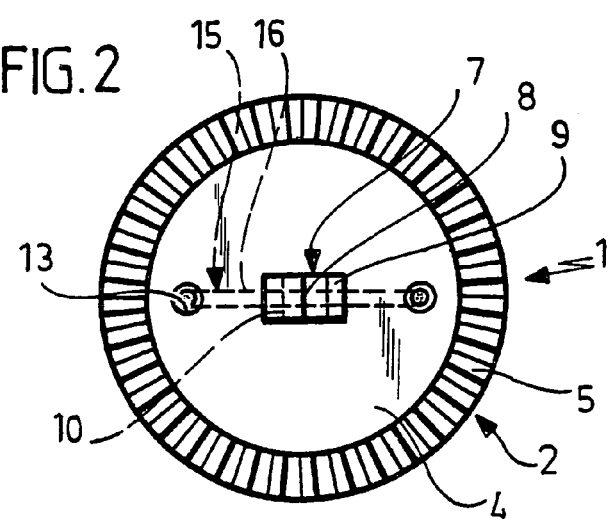

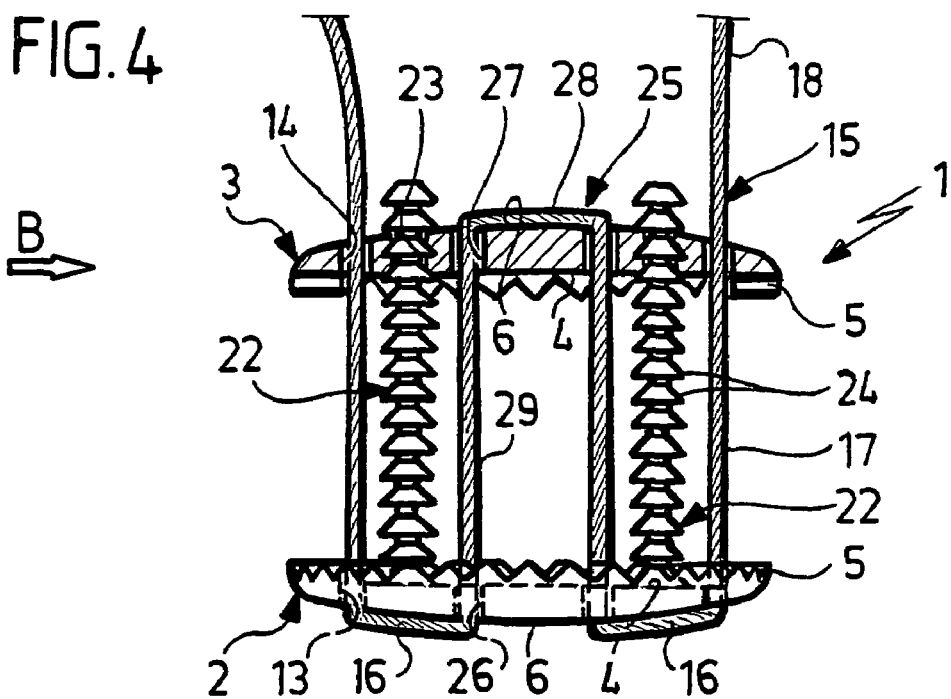
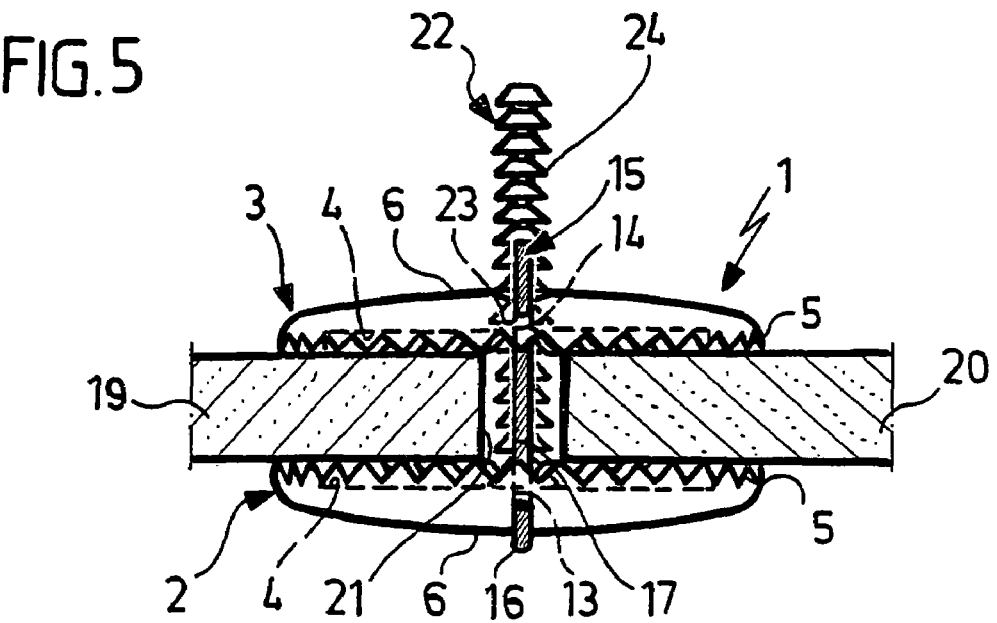

IMPLANT FOR FIXING BONE PLATES

The present disclosure relates to the subject matter disclosed in international application PCT/EP02/05653 of May 23, 2002 and disclosed in German application No. 101 28 917.0 of Jun. 15, 2001, which are incorporated herein by reference in their entirety and for all purposes.

BACKGROUND OF THE INVENTION

The invention relates to an implant for fixing neighbouring bone plates of the cranial bone, wherein said plates have an inner surface and an outer surface and the implant comprises an inner bearing element which covers a spacing gap between the bone plates, an outer bearing element which covers the spacing gap, and a connecting device which extends through the spacing gap and which, when the bearing elements approach one another, connects said bearing elements together by means of a latching or a clamping connection in such a manner that they are no longer able to be moved apart.

Implants of this type are known from the German utility model 29919090 for example. They are used in order to relocate bone plates in their original position within the cranial bone after they have been separated therefrom by means of a saw cut so that they can graft back in this position.

For this purpose, it is known to arrange plate-like bearing elements on both sides of the bone plates, which are only separated from one another by a spacing gap, and to connect them together by means of a central pin or a central locking strap. Moreover, rather than utilising latching or clamping means of this type, it is also known to simply draw the two plate-like bearing elements together by means of a thread-like tensioning element and to keep them clamped against one another by means of this thread-like tensioning element.

When using pin-like connecting means, it is necessary to clamp the two bearing elements together by means of a suitable tool which engages with the connecting device, which penetrates the outer bearing element and which simultaneously moves the outer bearing element along the connecting device in the direction of the inner bearing element. Such instruments are of complicated construction and are not always easy to manipulate.

If one uses a thread-like tensioning element for connecting the two bearing elements, then it is relatively easy to manipulate it when tensioning the bearing elements, but the result of this is that the connection between the bearing elements is very flexible and may sometimes give way in an undesirable manner in certain circumstances, for example, if the thread-like tensioning elements should work loose or if they dissolve in the case where a thread of resorbable material is being used.

SUMMARY OF THE INVENTION

In accordance with the present invention, an implant is provided with that, on the one hand, the application of the bearing elements and the process of clamping the bearing elements is executable in as simple a manner as possible whilst, on the other hand, it is intended that the two bearing elements should experience a reliable and durable connection when in the applied state.

In accordance with the invention, this is achieved in that the two bearing elements are additionally connected by means of a thread-like tensioning element which is passed through the outer bearing element in displaceable manner and, when tensioned, moves the inner bearing element towards the outer bearing element.

Thus, it is envisaged that the implant be provided with connecting means which connect the two bearing elements together in a durable and secure manner after they have been brought close together, and also thread-like tensioning elements, whose task consists essentially in tensioning the two bearing elements together during the application process so that the connecting means can thereby come into engagement.

The thread-like tensioning element can either be removed after the application process, or, it may be retained as an additional securing device for the two bearing elements, for example, the ends of such a thread-like tensioning element could be knotted together.

In a first preferred embodiment, provision is made for the tensioning element to be located at the inner bearing element so that the inner bearing element can then be pressed against the inner surfaces of the two bone plates by means of the tensioning element whilst the outer bearing element is simultaneously moved towards the inner bearing element in a latching or clamping manner.

Particularly preferred however is an exemplary embodiment wherein provision is made for the tensioning element to be passed through two openings in the inner bearing element and then be extended over the outer surface of the inner bearing element that is remote from the outer bearing element in the area between the openings. The tensioning element is thus guided in the form of a U-shaped loop, whereby the two ends of the tensioning element are passed through openings in the inner bearing element and, from there, extend through the spacing gap to the outer bearing element. It is expedient thereby, if the two ends of the tensioning element are passed through a respective opening in the outer bearing element.

It is expedient, if the two openings are spaced from one another by a distance which corresponds to at least half the elongation of the inner bearing element in the direction of interconnection. Consequently, the two ends of the tensioning element will engage with opposite outer surfaces of the inner bearing element, the bearing element thereby inevitably being aligned in such a way that the direction of connection of the two openings in the inner bearing element for the two ends of the tensioning element will extend in parallel with the direction of the spacing gap.

It is particularly advantageous, if the connecting device is arranged between the two sections of the tensioning element extending between the bearing elements. Due to the fact that the two ends of the tensioning element are fed between the two bearing elements such that they are mutually spaced, sufficient space will remain therebetween for arranging the connecting device there, for example, centrally.

Furthermore, it is advantageous if the dimensions of the connecting device in a direction transverse to the plane spanned by the sections of the tensioning element extending between the two bearing elements is small so as to enable said connecting means to pass through the spacing gap. The connecting device and the tensioning means are thus located essentially in one plane and extend only in this plane and as little as possible in the direction transverse to this plane so that the elements described can easily be passed through even a very narrow spacing gap, it thus being possible to move the bone plates that are to be connected relatively close to one another.

In a particularly preferred embodiment, provision is made for the tensioning element to be fed through the inner bearing element from the outer surface thereof in the form of a loop which extends through two mutually spaced openings in the outer bearing element so that, between these openings, the loop will rest upon the outer surface of the outer bearing element which is remote from the inner bearing element. As a result of this form of guidance of the thread, there will be a total of four sections of thread between the two bearing elements, i.e. a kind of pulley-block will be formed so that a displacement of the bearing elements corresponds to a shortening of the thread-like tensioning element, this accordingly being effected in a step-down ratio, although with greater power. Hereby, provision may be made for the openings for the loop and the openings for the ends of the tensioning element in the outer bearing element to lie along a straight line, and in particular, these openings are arranged to be mutually equidistant.

It is also advantageous hereby, if the loop extends through two mutually spaced openings in the inner bearing element. These openings too could also lie along a straight line together with the openings for the ends of the tensioning element and, in particular, be arranged such that they are mutually equidistant.

A particularly expedient arrangement, is one wherein the sections of the tensioning element extending between the bearing elements, the loop and the connecting device are arranged in one plane.

In a particularly preferred embodiment, the tensioning element may be freely displaceable in relation to both bearing elements and therefore adapted to be withdrawn from both bearing elements after they have been connected together by the connecting device.

It is also expedient, if the tensioning element consists of a material which is absorbable in the body.

In a preferred embodiment of the invention, provision is made for the connecting device to be arranged in the area between the bearing elements and not to project outwardly therethrough. Due to the use of the flexible clamping means, it then becomes possible to reliably clamp the bearing elements together even when the connecting device does not project outwardly through the outer bearing element.

For example, latching projections may be arranged on both bearing elements on the inner surfaces thereof facing the other bearing element, said latching projections engaging behind one another in latching manner when the bearing elements approach one another.

It is advantageous thereby, if two latching elements are arranged on a bearing element such as to be mutually adjacent, and if a latching element on the other bearing element engages between said adjacent latching elements in latching manner when the bearing elements approach one another.

A step-by-step latching process and thus adaptation to the thickness of the bone plates that are to be fixed together thereby become possible if at least one of the latching elements carries a plurality of latching projections.

In the case of another preferred embodiment, provision is made for at least two mutually adjacent connecting devices to be arranged on the bearing elements, said connecting devices having very small dimensions in a direction transverse to the plane defined thereby.

Thus here, in contrast to the known bearing elements which generally use a central connecting device, at least two such neighbouring connecting devices are used on the bearing elements, said connecting devices spanning a plane, and this plane passing through the spacing gap when the bearing elements have been applied. Due to the use of two connecting devices, the bearing element will be oriented relative to the bone plates in such a manner that this plane will extend in parallel relative to the spacing gap, it also being possible to fix the bearing elements in a non-parallel arrangement should this be necessary, i.e. in the event that this should be required due to different thicknesses of the bone plates that are to be connected.

Such an implant comprising two bearing elements that are connected to one another by two mutually adjacent connecting devices can also be used without the previously described thread-like tensioning means, the scope of protection extending expressly also to such an embodiment.

It is expedient, if the connecting devices comprise latching or clamping pins which are fixed to the inner bearing element and penetrate latching or clamping openings in the outer bearing element.

These latching or clamping openings may carry latching projections which co-operate with latching projections on the latching or clamping pins.

In another embodiment, provision is made for the latching or clamping openings to comprise resiliently deformable clamping members which co-operate with the surface of the latching or clamping pins. For example, these clamping members may be springy tongues which are bent out from the plane of the bearing elements when the latching or clamping pins are pushed through the latching or clamping openings, and the edges thereof rest on the surface of the latching or clamping pins in such a way that a relative displacement of the latching or clamping pins with respect to the bearing element is only possible in one direction.

The bearing elements and the connecting means are preferably manufactured in one-piece from a synthetic material.

The following description of the preferred embodiments serves, in conjunction with the drawing, to provide a more detailed explanation.

BRIEF DESCRIPTION OF THE DRAWINGS

FIG. 1: a side view of a first preferred exemplary embodiment of an implant incorporating a U-shaped thread-like tensioning element and having latching projections directed towards the respective other bearing element prior to the bearing elements being brought together;

FIG. 2: a sectional view along the line 2—2 in FIG. 1;

FIG. 3: a view of the implant of FIG. 1 in the direction of the arrow A in FIG. 1 after the application of the implant to two bone plates;

FIG. 4: a view similar to FIG. 1 of a further preferred exemplary embodiment of an implant comprising two mutually spaced connecting devices and a thread-like tensioning element in a multiple loop arrangement and FIG. 5: a view of the implant of FIG. 4 in the direction of the arrow B in FIG. 4 after the application of the implant to two bone plates.

DETAILED DESCRIPTION OF THE INVENTION

The implant 1 illustrated in FIGS. 1 to 3 incorporates two circular, plate-like bearing elements 2, 3 which comprise a serrated boundary region 5 on the flat, mutually facing inner faces 4 thereof and an external surface 6 which is slightly domed in the outward direction.

The inner bearing element 2 carries a central latching projection 7 which points towards the outer bearing element 3 and has a tip 8 with inclined glide surfaces 9. This latching projection 7 has an elongated rectangular cross section and the narrow sides thereof carry a number of latches 10, whilst the broad sides thereof are smoothly formed.

The outer bearing element 3 carries two mutually spaced latching projections 11 which point towards the inner bearing element 2 and are likewise provided with a number of latches 12 on the mutually facing narrow sides. These narrow sides incorporating the latches 12 are spaced from one another by a distance which corresponds to the width of the latching projections 7 on the inner bearing element 2. When the two bearing elements 2, 3 are moved close to one another, the free ends of the latching projections 11 slide on the inclined glide surfaces 9 of the latching projections 7 and are slightly flexed apart so that the latches 12 can slide past the latches 10. Hereby, the shaping of the latches 10 and 12 is selected in such a way that although it is possible for the bearing elements 2 and 3 to come close together, the two bearing elements 2, 3 will not be able to separate from each other following the engagement of the latches 10 and 12.

The latching projections 11 are also of rectangular cross-section and are provided with latch-free broad sides and narrow sides which carry the latches 12 in like manner to the latching projection 7. The latching projections 7 and 11 thus extend substantially in a plane which runs parallel to the broad sides of the latching projections 7 and 11, but they are of very small dimensions in the transverse direction, as is clear from the illustration in FIG. 3.

In this plane spanned by the latching projections 7 and 11, there are provided two openings 13 and 14 which penetrate the respective bearing elements, both the inner bearing element 2 and the outer bearing element 3, and which are mutually spaced by a distance which corresponds to at least the radius of the bearing elements 2, 3 and which are arranged symmetrically relative to the two sides of the respective latching projections 7 and 11. A thread-like tensioning element 15 is fed through these openings 13, 14 in such a manner that a central section 16 will rest against the outer surface 6 of the bearing element 2 between the openings 13 in the inner bearing element 2, whilst two connecting sections 17 will extend in parallel with the latching projection 7 from each opening 13 in the inner bearing element 2 to each opening 14 in the outer bearing element 3, the two ends 18 of the tensioning element 15 then extending through the openings 14 and continuing over the outer surface 6 of the outer bearing element 3 (FIG. 1).

The two bearing elements 2 and 3 preferably consist of a body-compatible synthetic material, whilst the latching projections 7 and 10 are formed in one-piece with the respective bearing elements 2 and 3. The thread-like tensioning element 15 may be a conventional surgical thread, it being expedient if it consists of an absorbable material which gradually decomposes after insertion into the body.

The described implant 1 serves for fixing two bone plates 19, 20 of the cranial bone which are to be fixed directly adjacent one another whilst leaving a spacing gap 21 therebetween. The spacing gap 21 is usually a saw-slot which is formed as a result of a bone plate being sawn out from the cranial bone. Consequently, one of the two bone plates is usually the solid bone plate of the skull, whilst the other bone plate is a sawn-out cranial bone which allowed access to be made to the brain. As is apparent from FIG. 1, for the purposes of fixing the two bone plates to one another, the implant 1 is firstly advanced towards a bone plate in such a way that the inner bearing element 2 will come to rest against the inner surface of the bone plate. The other bone plate is then introduced laterally into the intermediary space between the two bearing elements 2, 3 which are still spaced from one another, and the inner bearing element 2 is then clamped against the inner faces of the two bone plates 19, 20 with the help of the tensioning element 15. When the inner bearing element 2 is fixed in position, the outer bearing element 3 is pushed towards the inner bearing element 2 until such time as the respective latches 10 and 12 of the two latching projections 7 and 11 come into engagement with one another. This process of advancing the outer bearing element 3 can either be effected manually or by utilising an instrument, whereby the inner bearing element 2 will be held in place on the inner surface of the bone plates with the help of the tensioning element 15, or else by virtue of the two ends of the tensioning element 15 being drawn together, for example, by means of a known tensioning knot which is adapted to effect a shortening of the tensioning element 15 in the form of a loop extending through the openings 13 and 14, but not however, a prolongation thereof.

The latching projections 7 and 10 lie in the same plane as that in which the connecting sections 17 of the tensioning element 15 also extend, the dimensions of each of the parts in a direction transverse to this plane being very small so that these parts will easily fit into even a very narrow spacing gap 21, as is clear from the illustration in FIG. 3. At the same time, the latching projections 7 and 11 as well as the central section 17 of the tensioning element 15 will orient the two bearing elements 2, 3 in such a way that this plane runs parallel to the spacing gap 21.

If the two bearing elements 2, 3 are clamped together in this way, then they are securely held in this seating position, which is illustrated in FIG. 3, by the engagement of the latches 10 and 12. The tensioning element 15 can then either be removed by simply pulling it out of the openings 13, 14, or, it may be left in place as an additional security device, whereby it is expedient to knot the two ends 18 to one another.

In the case of the implant illustrated in FIGS. 1 to 3, the connecting means of the two bearing elements 2, 3 formed by the latching projections 7 and 11 do not project therethrough, but rather, they merely extend through the space in the spacing gap 21.

This is not the case in the exemplary embodiment of an implant illustrated in FIGS. 4 and 5, although this is of similar construction and the mutually corresponding parts thereof bear the same reference symbols. In the case of the implant in FIGS. 4 and 5, the inner bearing element 2 has two mutually spaced, parallel connecting pins 22 which extend symmetrically relative to the centre point and protrude through apertures 23 in the outer bearing element 3. The connecting pins 22 carry peripheral latching ribs 24 which are bevelled at one side and can be pushed through the apertures 23 in one direction, but, in the opposite direction, the latching ribs engage and latch behind the edges of the apertures 23 in such a manner that it is no longer possible to pull the bearing elements 2 and 3 apart. The edges of the apertures 23 are thus latching projections which co-operate with the latching ribs 24.

The connecting pins 22 are arranged in the plane which is defined by the openings 13 and 14 for the tensioning element 15, and they are of very small diameter so that the connecting pins 22 exhibit only a very small dimension in a direction transverse to this plane and thus this implant 1 too, together with the tensioning element 15 and the two connecting pins 22, can also be fitted into a very narrow spacing gap 21.

Moreover, in the case of the exemplary embodiment of FIGS. 4 and 5, the central area of the tensioning element 15 is in the form of an additional loop 25, thus deviating from the shape of the implant depicted in FIGS. 1 to 3. Namely, this loop 25 passes through two openings 26 located between the openings 13 in the inner bearing element 2 and through two openings 27 arranged between the openings 14 in the outer bearing element 3, so that the central section 28 of this loop 25 rests on the outer surface 6 of the outer bearing element 3. The openings 26 and 27 are thereby located closer to the centre of the respective bearing elements 2 and 3 than the apertures 23 so that two further connecting elements 29 now extend between the two connecting pins 22 in addition to the connecting sections 17 of the tensioning element 15, these forming the legs of the loop 25 and lying in the same plane as the connecting sections 17 and the connecting pins 22. This thereby results in a pulley-block-like guidance of the tensioning element 15 so that, when tensioning the latter, the displacement path of the bearing elements 2, 3 will be scaled down with respect to the tensioning path of the tensioning element 15.

This guidance of the tensioning element 15 is particularly advantageous in an arrangement comprising two mutually spaced connecting means such as is formed by the connecting pins 22, but use could also easily be made of differently constructed bearing elements 2, 3 wherein other forms of connecting means are provided.

It is also expedient in the case of the exemplary embodiment depicted in FIGS. 4 and 5, if the connecting pins 22 are formed in one-piece with the bearing elements 2, 3, whereby these preferably consist of a body-compatible synthetic material. Here too, the tensioning element 15 may be made of an absorbable material.

The invention claimed is:

1. An implant for fixing neighboring bone plates of a cranial bone, wherein said plates have an inner surface and an outer surface and the implant comprises:
    an inner bearing element which covers a spacing gap between the bone plates,
    an outer bearing element which covers the spacing gap,
    a connecting device which extends through the spacing gap and which, when the bearing elements are moved towards one another, connects said bearing elements together by means of a latching or a clamping connection such that the bearing elements are no longer able to be moved apart, and
    a thread-like tensioning element which is passed through the outer bearing element in a displaceable manner and, when tensioned, moves the inner bearing element towards the outer bearing element forming an additional connection between the two bearing elements.

2. An implant in accordance with claim 1, wherein the tensioning element is located at the inner bearing element.

3. An implant in accordance with claim 1, wherein the tensioning element is passed through two openings in the inner bearing element and extends over an outer surface of the inner bearing element that is remote from the outer bearing element in an area between the openings.

4. An implant in accordance with claim 3, wherein each of two ends of the tensioning element are passed through a respective opening in the outer bearing element.

5. An implant in accordance with claim 3, wherein the two openings in the inner bearing element are spaced from one another by a distance which corresponds to at least half a length of the inner bearing element in a direction of interconnection.

6. An implant in accordance with claim 3, wherein the connecting device is arranged between two sections of the tensioning element extending between the bearing elements.

7. An implant in accordance with claim 6, wherein dimensions of the connecting device in a direction transverse to a plane spanned by the sections of the tensioning element extending between the two bearing elements ae small to enable the passage of the connecting device through the spacing gap.

8. An implant in accordance with claim 3, wherein the tensioning element is fed through the inner bearing element from the outer surface thereof in the form of a loop which extends through two mutually spaced openings in the outer bearing element so that, between these openings, the loop rests on the outer surface of the outer bearing element which is remote from the inner bearing element.

9. An implant in accordance with claim 8, wherein the openings for the loop and openings for ends of the tensioning element in the outer bearing element lie along a straight line.

10. An implant in accordance with claim 8, wherein the openings for the loop and openings for ends of the tensioning element are mutually equidistant.

11. An implant in accordance with claim 8, wherein the loop extends through two mutually spaced openings in the inner bearing element.

12. An implant in accordance with claim 11, wherein the openings for the loop and openings for ends of the tensioning element in the inner bearing element lie along a straight line.

13. An implant in accordance with claim 11, wherein the openings for the loop and openings for ends of the tensioning element in the inner bearing element are mutually equidistant.

14. An implant in accordance with claim 8, wherein sections of the tensioning element extending between the bearing elements, the loop and the connecting device are arranged in a plane.

15. An implant in accordance with claim 3, wherein the tensioning element is freely displaceable in relation to both bearing elements and is adapted to be withdrawn from both bearing elements after they have been connected by the connecting means.

16. An implant in accordance with claim 1, wherein the tensioning element consists of a material that is absorbable in the body.

17. An implant in accordance with claim 1, wherein the connecting device is arranged in an area between the bearing elements and does not project outwardly through the bearing elements.

18. An implant in accordance with claim 17, wherein latching projections are arranged on both bearing elements on inner surfaces thereof facing the other bearing element, said latching projections engaging behind one another in a latching manner when the bearing elements are moved towards one another.

19. An implant in accordance with claim 18, wherein two mutually adjacent latching elements are arranged on one of the bearing elements, and wherein a latching element on the other bearing element engages between said adjacent latching elements in latching manner when the bearing elements are moved towards one another.

20. An implant in accordance with claim 18, wherein at least one of the latching elements carries a plurality of latching projections.

21. An implant in accordance with claim 1, wherein at least two mutually adjacent connecting devices are arranged on the bearing elements, said connecting devices having small dimensions in a direction transverse to a plane defined by the connecting devices.

22. An implant in accordance with claim 21, wherein the connecting devices comprise latching or clamping pins which are fixed to the inner bearing element and penetrate through latching or clamping openings in the outer bearing element.

23. An implant in accordance with claim 22, wherein the latching or clamping openings carry latching projections which co-operate with latching projections on the latching or clamping pins.

24. An implant in accordance with claim 22, wherein the latching or clamping openings comprise resiliently deformable clamping members which co-operate with a surface of the latching or clamping pins.

25. An implant in accordance with claim 1, wherein the bearing elements and the connecting device are formed in one-piece from a synthetic material.

* * * * *